United States Patent [19]

Strickland et al.

[11] 4,253,461
[45] Mar. 3, 1981

[54] ABSORBENT BRIEF

[75] Inventors: Danny L. Strickland; Ronald B. Visscher, both of Cincinnati, Ohio

[73] Assignee: The Procter & Gamble Company, Cincinnati, Ohio

[21] Appl. No.: 83,747

[22] Filed: Oct. 11, 1979

Related U.S. Application Data

[63] Continuation of Ser. No. 829,035, Aug. 30, 1977, abandoned.

[51] Int. Cl.³ .............................................. A61F 13/16
[52] U.S. Cl. ............................. 128/287; 128/DIG. 30
[58] Field of Search ........ 128/287, 284, 270, DIG. 30

[56] References Cited

U.S. PATENT DOCUMENTS

| | | | |
|---|---|---|---|
| 2,119,610 | 6/1938 | Tasker | 128/284 |
| 2,834,347 | 5/1958 | Connolly | 128/284 |
| 2,936,758 | 5/1960 | Csulits | 128/284 |
| 3,349,769 | 10/1967 | Piekarski | 128/284 |
| 3,417,751 | 12/1968 | Murdoch | 128/287 |
| 3,452,753 | 7/1969 | Sanford | 128/287 |
| 3,509,881 | 5/1970 | Sabee | 128/287 |
| 3,828,785 | 8/1974 | Gamm et al. | 128/288 |
| 3,860,003 | 1/1975 | Buell | 128/287 |
| 3,920,018 | 11/1975 | Schear | 128/DIG. 30 |
| 4,018,226 | 4/1977 | Korgemets | 128/287 |
| 4,034,752 | 7/1977 | Tritsch | 128/284 |
| 4,037,602 | 7/1977 | Hawthorne | 128/284 |
| 4,050,462 | 9/1977 | Woon et al. | 128/287 |
| 4,069,822 | 1/1978 | Buell | 128/287 |

FOREIGN PATENT DOCUMENTS 1435852 2/1969 Fed. Rep. of Germany .......... 128/287
1444925 8/1976 United Kingdom ..................... 128/287

Primary Examiner—Robert W. Michell
Assistant Examiner—C. W. Shedd
Attorney, Agent, or Firm—Fredrick H. Braun; Richard C. Witte

[57] ABSTRACT

A disposable absorbent brief having substantially straight parallel elastic members on either side of the crotch and separate means to secure the brief to the wearer's thighs and to the wearer's waist, said brief being especially adapted for use by wearers having adult leg configurations. The securement means which forms a thigh seal is placed within an anchoring region of the brief comprising the area between the edge of the brief and two line segments which lie transversely outward of the elastic member and which form angles of about 90 and about 140 degrees, respectively, in the plane of the diaper with respect to the elastic member. The apex of these angles is at one functional endpoint of the elastic member. When the brief is worn the elastic member, the securement means, and portions of the material of the brief cooperate to form a fluid-stopping seal around the thigh of the wearer, said seal being located substantially within a plane perpendicular to the thigh bone of the wearer as that plane is defined hereinafter.

1 Claim, 3 Drawing Figures

ABSORBENT BRIEF

This is a continuation of application Ser. No. 829,035 filed Aug. 30, 1977, now abandoned.

BACKGROUND OF THE INVENTION

This invention relates generally to improvements in a disposable absorbent garment intended to be used to receive or tending to receive discharge from the body, and in particular relates to disposable diapers, incontinent pads, and the like designed to be worn on the body and having a contractable thigh-encircling portion which conforms to the contours of the body and permits movement of the body while maintaining a seal with the body in motion. This invention further relates to means to secure such a garment to the body of the wearer and more particularly to means adapting the thigh-encircling portions of said garment to an adult leg configuration.

Absorptive devices such as disposable incontinent briefs are well-known in the art. These devices are used to absorb liquid from the human body and retain that liquid until the garment can be disposed of. Present disposable incontinent briefs are frequently flat composite sheets which are fitted to a wearer in the flat state or incorporate geometric folding to achieve a suitable body shape. A major in-use problem with such prior art articles is that gaps between the brief and the wearer's legs tend to develop due to the semi-rigid nature of the absorbent body, especially after the brief has been worn for some time, or during a period of activity when the garment is able to flex or shift on the wearer's body. These gaps permit leakage from a disposable garment, thereby creating damp outer clothing or bedding around the wearer.

Although these problems have been alleviated somewhat in the case of infant's diapers, the fitting of such a garment to an adult presents problems not found in the creation of a garment suitable for an infant.

First, since the legs of an infant characteristically form a substantial angle with the lateral line of the trunk of the body, it has been observed that a diaper having straight-line elastics such as those described in U.S. Pat. No. 3,860,003 issued to Buell on Jan. 14, 1975, can be secured to the infant's body by a single securement means on either side of the diaper. This is true because a circle drawn around the top portion of the diaper on the baby's body and a circle drawn around the thigh seal portion very nearly intersect at one tangent point, so that a single securement means placed at that point will effectively secure the waist and the thigh portions of the diaper simultaneously. However, in an adult, whose legs in the normal position are generally substantially parallel to each other and to the lateral line of the trunk of the wearer's body, a circle drawn at the edge of the garment about the wearer's thigh and substantially perpendicular to the wearer's thigh as defined hereinafter does not at any point approach a second circle drawn around the top portion of the garment secured about the wearer's waist or trunk. Thus, unlike prior art devices primarily designed to fit an infant, a single securement means on each side of the article will not serve to conform the garment to an adult wearer's waist while effectively securing the garment against leakage at the thigh area.

Second, as also revealed in the aforementioned Buell patent, it is desirable to construct an incontinent brief with elastics which are parallel to each other, and which lie along each edge of the crotch. This simplifies the manufacture of an incontinent brief, since the elastic can be applied in the machine direction when the article is manufactured. Brief elastics having a substantially straight-line contractable dimension have advantages in use as well. A substantially straight-line elastic member in the region of the crotch allows a single article to contract substantially along this dimension, so that the differing crotches of various individuals are accommodated to provide a snug fit of the article in the crotch area of the wearer. (This development of the prior art is in contrast to a great number of similar articles, such as conventional underwear, deploying elastic members which have no substantial straight-line element, and which generally conform around a cut-out in the brief.) However, a corresponding problem in prior art structures employing parallel straight-line elastic members having a substantially longitudinal contractable dimension and a single securement means to secure the waistband and legband portions, especially in an adult garment where the crotch width must necessarily be much less than the width of the portion of the garment which wraps around the trunk of the wearer, is that one cannot draw the functional ends of the straight-line elastic member effectively together around the thigh of the wearer to form a seal which is substantially perpendicular (as defined hereinafter) to the thigh bone of the wearer without unduly compromising the fit of the waistband portion about the wearer's trunk. As pointed out above, a seal which is not substantially perpendicular to the thigh bone of the wearer will not adequately contain the material which is to be absorbed or held by the brief.

In summary, devices can be found in the prior art which have straight-line elastic members on either side of the crotch; prior art structures having roughly the same can be found wherein a plurality of fasteners are used on either side of a garment to attach it to the body of a wearer. However, prior art is not available to solve the specific problems which are encountered when straight-line elastic members are used in a garment which requires a plurality of fastening means on either side of the body of the wearer in order to seal the garment to the thigh while providing a fit to the trunk of the wearer as well.

SUMMARY OF THE INVENTION

The present invention lies in the provision of an improved thigh seal in a disposable absorbent brief particularly adapted to an adult wearer, as defined hereinafter, and having substantially straight-line elastic portions in the crotch area thereof. This seal, which is not elasticized around its entire perimeter when the brief is in use, is facilitated by placement of the anchored portion of a thigh securement means on an anchoring region of the brief surface located intermediate two line segments lying respectively on the transversely outward legs of two angles having their apexes at one functional endpoint of the brief elastic, the first angle being about 90 degrees transversely outward with respect to the elastic member, and the second angle being about 140 degrees transversely outward with respect to the same elastic member, said anchoring portion of the brief surface being bordered on its third side by the edge of the brief at a lower part of the trunk-encircling portion.

When the brief is donned by encircling the thigh of the wearer with the lower part of one trunk-encircling portion of the brief, the user-actuated portion of a securement means which is already anchored on the anchoring portion as above defined is further secured to the lower part of the second trunk-encircling portion of the brief in a position effective to achieve the desired seal. The site of attachment of the user-actuated portion of the lower securement means is somewhere on the backsheet of the second trunk-encircling portion, the exact site depending on the particular thigh, trunk, and crotch dimensions of the weearer.

As a result of the critical placement of the anchored portion of the thigh securement means on the indicated segment of the brief, a seal is generally defined by the following structures: the elastic member; a portion of the brief material lying along a tensioned line between the functional endpoint of the elastic member which defines the apexes described above and the anchored portion of the thigh securement means; and the user-actuated portion of the thigh securement means. If the user-actuated portion of the thigh securement means is attached to the brief transversely outward of the elastic member, the portion of brief material between that point of attachment and the second functional end of the elastic forms a portion of the seal as well. It is of the essence in this invenion that the elements of the seal defined above lie substantially in a plane perpendicular, as defined hereinafter, to the thigh bone of the wearer when the brief is in use.

It should be noted that while the brief requires further means to conform it about the trunk of the wearer, such means are known in the art and are not within the scope of this invention.

OBJECTS OF THE INVENTION

The objects of this invention are to solve the problems noted in the prior art, as well as to provide an incontinent brief with an improved thigh seal, suitable for use by adults and capable of being worn under the clothing of an adult as well as by an adult who is bedridden. Further objects of the invention will become apparent from the description following.

BRIEF DESCRIPTION OF THE DRAWINGS

While it is believed that the invention will be better understood from the description appearing below of preferred embodiments of the present invention, it is understood that the invention herein is defined by the claims which particularly point out and distinctly claim the subject matter which is regarded as forming the present invention.

DETAILED DESCRIPTION OF THE INVENTION

For the purposes of this specification, an "adult" is defined as any person having thigh bones which are oriented substantially parallel to the lateral line of the body during a majority of the wearer's activities. This distinguishes an "adult" from an infant, and particularly from an infant who has not yet learned to walk, for the legs of such an infant usually form a substantial angle with respect to the lateral line of its body during a majority of the wearer's activities. Thus an "adult" as defined herein may include youths and teenagers who have leg orientations similar to those of a mature person.

A plane which is "substantially perpendicular" to the thigh-bone of the wearer is defined herein as a plane forming a plane angle of between about 0 degrees and about 40 degrees with respect to a plane which is geometrically perpendicular to the thigh-bone of the wearer.

Figure 1:
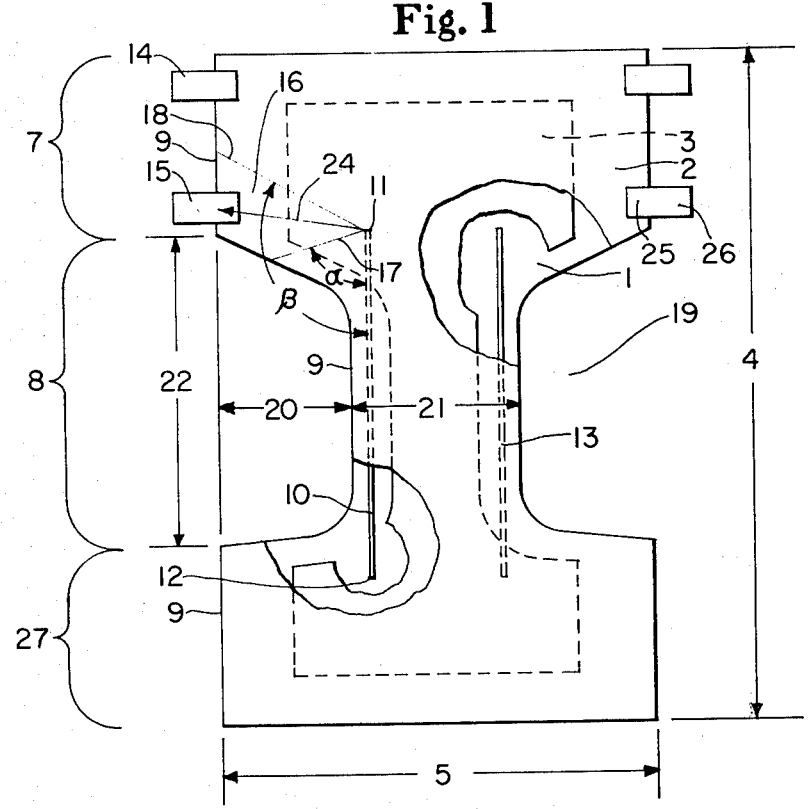
FIG. 1 is a plan view of a preferred embodiment of the invention with its elastic members in an extended condition and the wearer contacting portion of the brief facing the viewer.
Figure 2:
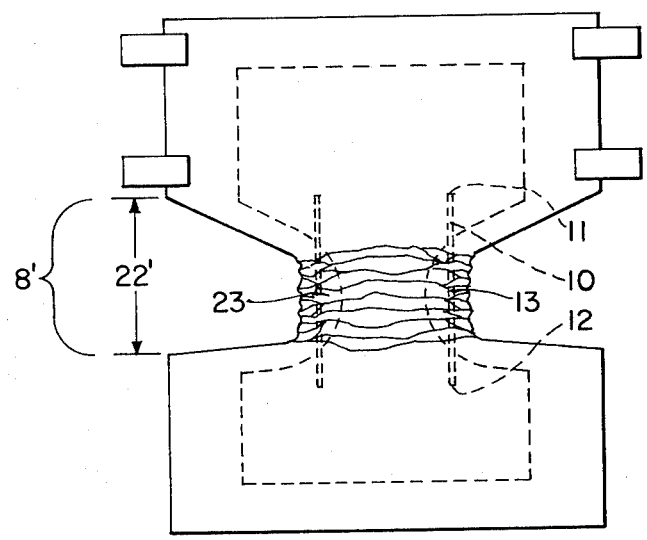
FIG. 2 is a plan view of the device of FIG. 1, illustrating a preferred embodiment of the invention, with the elastic in an unstressed condition.

FIGS. 1 and 2 represent a particularly preferred embodiment of the present invention having side notches which receive the legs of the wearer in order to provide a brief having a well-tailored contour when it is worn.

The absorbent brief forming the present invention is comprised generally of moisture-impervious backsheet 1, moisture-pervious topsheet 2, and moisture-absorbent member 3 therebetween. The backsheet 1 and topsheet 2 are preferably secured to one another about absorbent member 3 at the periphery of the article which is generally indicated by 9.

The dimensions of the brief of FIG. 1 are more particularly described by a longitudinal dimension 4, a transverse dimension 5, a crotch portion 8 having a crotch length 22, a crotch width 21, a cut-out width 20, and trunk-encircling portions 7 and 27. It is to be understood that the diaper may be worn with either trunk-encircling portion 7 or trunk-encircling portion 27 forward, although in the preferred mode of use the trunk-encircling portion 7 forms the rear portion of the garment when it is worn. Crotch portion 8 of the article is provided with a plurality of elastic members 10, preferably one on each side of the wearer's crotch, and generally disposed near the edge of the garment. Each elastic member 10 has endpoints 11 and 12, hereinafter referred to as "functional endpoints" because it is appreciated that an end portion of elastic member 10 may be provided which is unable to gather or shirr the garment because it is either stiffened or unadhered to the article.

Absorbent member 3 of the brief can be made of any of the absorbent materials known to those of ordinary skill in the bandage art. For example: a multiplicity of plies of creped cellulose wadding; fluffed cellulosic fibers or air-laid wood pulp fibers sometimes known as airfelt; textile fibers or other absorbent material. A particularly preferred absorbent member 3 may be constructed following the teachings of U.S. Pat. No. 3,860,003 (the Buell patent) which is hereby incorporated herein by reference. While in the embodiment of FIG. 1 absorbent member 3 lies generally between elastic members 10 in the crotch portion of the brief it is to be appreciated that this is not a requirement of the present invention, so long as elastic members 10 are able to contract the brief.

Moisture-impervious backsheet 1 is preferably a flexible moisture-impermeable sheet comprised of a low density, oqaque polyethylene web having a thickness of about 1 mil, such as the backsheet employed n the aforementioned Buell patent. In the embodiment illustrated in FIG. 1, the backsheet 1 has a rectangular configuration with leg cut-out areas 19 deviating from the rectangular configuration. In this embodiment the backsheet 1 extends beyond the periphery of the absorbent body around the entire periphery thereof. Brief side portion defined generally by the periphery of the backsheet extending beyond absorbent member 3, is roughly four inches wide in the trunck-encircling portions 7 and 27 and approximately and and one-half to two inches wide in the crotch portion 8 of the brief.

Topsheet 2 is coextensive in area with backsheet 1. One preferred embodiment of topsheet 2 is shown and described in U.S. Pat. No. 3,929,135 issued to Hugh Thompson on Dec. 30, 1975, said patent being hereby incorporated herein by reference. However, it is to be understood that the invention does not require a particular type of topsheet, or any topsheet at all.

The elastic member 10 is operatively associated with crotch portion 8 adjacent to brief side portion 9 in an elastically contractable condition so that in a normally unrestrained configuration, the elastic member 10 effectively contracts or gathers the crotch material to provide an elastic retraction line 13 colinear with the material of elastic member 10. Attachment of the elastic members 10 to achieve this result is also described in the aforementioned Buell patent.

A comparison between FIGS. 1 and 2 will illustrate the function of the elastic members 10 on either side of the crotch to adjust the length of the crotch to fit the body of a wearer. In FIG. 1, wherein the elastic members are stretched so that the entire garment lies substantially in a plane, crotch portion 8 has a maximized crotch length dimension 22. On the other hand, in FIG. 2, where the elastic is allowed to relax insofar as relaxation is permitted by the material of the brief, the crotch length dimension ' is roughly one-half as large as the identical dimension in FIG. 1. The exact variance between the dimensions 22 and 22' will depend on how the side-notch and crotch are dimensioned in a particular garment. As depicted by the reference numeral 23, the material in the crotch is gathered in FIG. 2, but the width 21 of the crotch is substantially unchanged between the two Figures. It has been found that when the crotch is elastically contractable in its longitudinal direction without substantial transverse contraction, the brief is well-suited to accommodate a wide range of sizes without the need for measurements or mechanical adjustments.

The effective length of elastic member 10 in its stretched condition is that length available to contract. The extremities of this effective length of elastic are defined by functional endpoints 11 and 12. These functional endpoints 11 and 12 may be distinguished from the actual endpoints of the elastic, for it is apparent that portions of the elastic may be so secured to the brief that they are unable to contract, or loose ends of the elastic may be allowed which do not contribute to the contraction of the brief.

Upon securement means 14 may provided by any of a number of means well-known in the art, such as tapes, an elastic band to which both ends of the brief are attached (analogous to the waistband of conventional underwear), snaps, pins, and so forth. Likewise, it is to be appreciated that lower securement means 15 can be any securement means which can be used to attach two portions of the garment together while it is being worn. One particularly preferred fastening means is the tape fastening structure generally disclosed in U.S. Pat. No. 3,848,594 issued to Buell on Nov. 19, 1974, said patent being hereby incorporated herein by reference.

A critical feature of the present invention is the placement of lower securement means 15. Lower securement means 15 is anchored by a manufacturer's joint at its anchored portion 25 to the brief within anchoring region 16, which is defined by the edge portion of the brief 9 and by line segments 17 and 18. First line segment 17 is bounded at its transversely inward end by functional endpoint 11 of the elastic member 10, and extends transversely outward from functional endpoint 11 in the plane of the brief at an angle $\alpha$ with respect to elastic member 10. Second line segment 18 similarly is bounded by functional endpoint 11 and extends transversely outward to the edge portion 9 of the brief in the plane of the brief at an angle $\beta$ with respect to elastic member 10. The angle $\alpha$ is preferably about 90 degrees, and the angle $\beta$ is preferably about 140 degrees when the elastics are located within about one and one-half inches of the lateral edge of the crotch portion of the diaper along a majority of their length. Particularly preferred values of $\alpha$ and $\beta$ are about 116 degrees and about 125 degrees, respectively.

When lower securement means 15 is anchored in region 16, securement vector 24, a tension vector, defines a portion of the brief between lower securement means 15 and functional endpoint 11 which lies approximately in a plane which is substantially perpendicular to the thigh of the wearer when the brief is worn, forming a part of the thigh seal.

To attach the brief to the body of the wearer, the brief is placed around the crotch and trunk portions of the wearer, upper securement means 14 is brought laterally around the trunk of the wearer and secured to the other side of the brief somewhere along the upper part of trunk-encircling portion 27. Similarly, lower securement means 15 is secured to the lower part of trunk-encircling portion 27. The points of securement of upper and lower securement means 14 and 15 are thus variable, depending on the particular body dimensions of the wearer in comparison to the dimensions of the brief.

When the garment is donned and attached as described above, elastic member 10 lies along the inner portion of the thigh of the wearer, and securement vector 24 lies along a second portion of the wearer's thigh. If the point of attachment of the user-actuated portion 26 of lower securement means 15 on trunk-encircling portion 27 is transversely inward of the line defined by elastic member 10, securement vector 24 overlies that line and is held in that overlying relation by circumferential tension to complete the seal. On the other hand, if the point of attachment of the user-actuated portion 26 of lower securement means 15 is transversely outward of a line defined by elastic member 10, the material of the garment spanning the space between said point of attachment and functional endpoint 12 of elastic member 10 completes the seal. When the brief is worn, these portions of the seal are all approximately on a plane which is substantially perpendicular to the thigh-bone of the wearer, and form a substantially unbroken seal around the thigh of the wearer. This thigh seal is resilient due to the action of elastic member 10, which contracts along elastic retraction line 13 to conform the seal to the thigh of the wearer. Thus, this structure satisfies the objects of this invention to provide a thigh seal which lies approximately in a plane which is substantially perpendicular to the thigh-bone of the wearer.

Briefs made according to this preferred embodiment of the invention can conveniently be made in small, medium and large sizes to accommodate the proportions of a wide number of consumers. A medium-sized brief adapted to fit the ordinary range of adult wearers having hip circumferential measurements in the range of about 32 inches to 44 inches can be accommodates by a brief having a functional stretched elastic length of about 8–9 inches, a longitudinal dimension 4 of about 33 inches, a transverse dimension 5 of about 25 inches, a crotch width 21 of about 9½ inches, and spacing between elastic members 10 across the crotch of about 8 inches. To accommodate the dimensions of a small adult or teenage wearer, a brief may conveniently be dimensioned with a functional stretched elastic length of about 8–9 inches, a longitudinal dimension 4 of about 28 inches, a transverse dimension 5 of about 18 inches, a crotch width 21 of about 7 inches, and spacing between elastic members 10 of about 6 inches across the crotch. A brief for large adults may conveniently have the following dimensions: a functional stretched elastic length of about 8–9 inches, a longitudinal dimension 4 of about 40 inches, a transverse dimension 5 of about 31 inches, a crotch width 21 of about 9½ inches, and a spacing between elastic members 10 of approximately 8 inches. While it is to be appreciated that the invention is not limited to embodiments having these dimensions, it has been found that these three brief sizes will accommodate a selection of wearers ranging from adolescents to rather large adults.

When a brief constructed in accordance with the above "medium" dimensions was worn by a particular female model, it was found that the separation between an upper tape, located with its center about an inch below the top of the brief, and the center of the thigh securement tape was about 5½ inches when an acceptable thigh seal was formed. When the thigh seal was optimized, the tape separation for this wearer ranged between about 6 inches and 8 inches. Within this range, the angle of the plane of the seal with respect to a plane perpendicular to the thigh-bone varied between about 20 degrees and about 30 degrees. When the angle of the plane of the seal exceeded about 40 degrees, the seal was no longer adequate. These figures for a single wearer are not intended to be descriptive of the entire range of brief wearers, but they illustrate that a brief designed for adult wear must have independent means to respectively secure the garment at the thigh and at the waist.

The optimum angle of the plane of the seal with respect to a plane perpendicular to the thigh of the wearer is an accommodation between the frequently conflicting goals of providing an effective thigh seal and providing a desirable overall fit of the brief to the wearer's body. The ideal angle from a sealing standpoint is nearly 0 degrees, at which point the circumference of the seal is minimized. The ideal angle from a fit standpoint would be much larger for many persons to form an ideal brief-shaped garment. The angles encompassed by the definition of "substantially perpendicular" in this specification represent the middle ground of configurations which will seal adequately while providing an acceptable fit.

Figure 3:
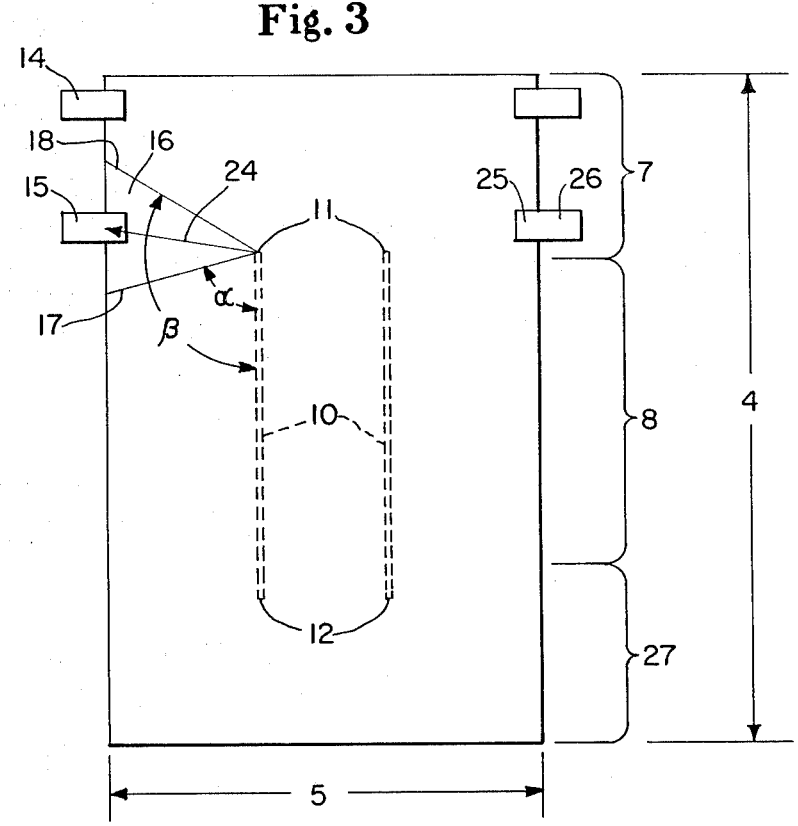
FIG. 3 is a plan view of an alternate embodiment of the invention, with its elastic members in an extended condition, and with its wearer contacting portion facing the viewer.

FIG. 3 shows an alternate, but less preferred embodiment of the invention wherein cut-out 19 is attenuated or eliminated from the brief. It will be appreciated that this embodiment will only work if portions of the brief material transversely outward of elastic member 10 will gather in response to retraction of elastic members 10 along elastic retraction lines 13 and will fold when the brief is worn so that the seal as described for the preferred embodiment of the invention will not be hindered by the presence of this material. It will further be appreciated that the general overall shape of the brief may be modified substantially in other ways from the preferred embodiment without departing from the scope of the invention, which is defined by the claims. The most preferred values of $\alpha$ and $\beta$ for this embodiment are about 125 degrees and about 132 degrees, respectively when the elastics are located within about 8½ inches of the lateral edge of the crotch portion of the diaper along a majority of their length. As this distance is decreased, the included angle ($\beta$-$\alpha$) generally increases.

What is claimed is:

1. In an absorbent brief having a moisture-impervious backsheet, a moisture pervious topsheet and a moisture-absorbent member interposed between said backsheet and said topsheet, the backsheet and topsheet having substantially identical rectangular configurations with oppositely disposed leg cut-out areas in the central portion of each side edge, the leg cut-out areas defining a crotch portion interposed and integrally joined with trunk-encircling portions at opposite ends of the brief, an elastic member joined to each side of the crotch portion, said elastic member being in contractable condition when joined thereby causing the crotch portion of the brief to have a tendency to gather, each of said elastic members extending through the crotch portion in a straight line and terminating in functional endpoints in the end area of the trunk-encircling portions nearest the crotch portion, upper securement means including a tape attached to and extending from each side edge of one of the trunk-encircling portions near the end edge thereof, the improvement comprising:

(a) lower securement means including a tape attached to and extending from each side edge of said one of said trunk-encircling portions,
   (b) each of said lower securement means being spaced inwardly toward the crotch portion with respect to said upper securement means,
   (c) each of said lower securement means being attached to an anchoring region,
   (d) each of said anchoring regions being defined by a side edge of the brief and two line segments, each of said line segments extending from the functional endpoint nearest each lower securement means of each of said elastic members to the nearest side edge of the brief,
   (e) the first of said line segments extending outwardly from the functional endpoint at an angle of at least about 90° as measured from the elastic member terminating at said functional endpoint,
   (f) the second of said line segments extending outwardly from the functional endpoint at an angle no greater than about 140° as measured from the elastic member terminating at said functional endpoint,
   (g) a securement vector lying within each of said anchoring regions and extending from said functional endpoints to the lower securement means,
   (h) whereby the lower securement means when attached to the opposite trunk-encircling portion when said brief is in use functions to form an effective thigh seal snugly around each leg of a wearer in a plane substantially perpendicular to the thigh-bone of the wearer.
   (i) the line of each of said thigh seals being through its respective elastic member, securement vector and lower securement means.

* * * * *

UNITED STATES PATENT AND TRADEMARK OFFICE
CERTIFICATE OF CORRECTION

PATENT NO. : 4,253,461
DATED : March 3, 1981
INVENTOR(S) : DANNY L. STRICKLAND, RONALD B. VISSCHER It is certified that error appears in the above-identified patent and that said Letters Patent are hereby corrected as shown below:

Column 4, line 63, "n" should read -- in --.

Column 5, line 1, after "portion" there should be -- 9, --.

Column 5, line 5, the second "and" should read -- one --.

Column 5, line 32, before the apostrophe there should be -- 22 --.

Column 5, line 55, "Upon" should read -- Upper --.

Column 5, line 55, after "may" there should be -- be --.

Column 7, line 4, "accommodates" should read -- accommodated --.

Signed and Sealed this

Nineteenth Day of January 1982

[SEAL]

Attest:

GERALD J. MOSSINGHOFF

Attesting Officer

Commissioner of Patents and Trademarks